United States Patent

Plant Pat. 3,870
Patented Apr. 20, 1976

3,870
GRAPEVINE

Harold P. Olmo, Davis, Calif., assignor to The Regents of the University of California, Berkeley, Calif.

Filed Feb. 3, 1975, Ser. No. 546,383
Int. Cl. A01h *5/03*
U.S. Cl. Plt.—47 1 Claim

This invention relates to a new and distinct variety of grapevine of the *vinifera* species to be used for the production of red table wine and port wine.

The principal varieties grown for red table wine production in the hotter regions of the Central Valley of California are Carignane and Grenache. Although reliable producers, the wines produced often lack color, body and flavor and must be ameliorated by blending with other varieties. Neither varietal wine improves much in aging and must be consumed when relatively young. The Carignane also fails to produce sufficient sugar in some seasons and is very subject to powdery mildew. The Grenache is sensitive to climatic change, the flowers may set poorly and the fruit at harvest time spoils easily if rained upon.

This new variety issued from the same progeny that produced the "Carnelian," Plant Pat. 3,625 dated Sept. 24, 1974. A selection from a cross made at Davis, Calif. in 1936 between Carignane × Cabernet-Sauvignon produced a female variety F2–7. This was used to cross with the Grenache in 1949. This new variety was then successfully asexually reproduced by budding it onto older vines and the reproductions carry forward all of the novel characteristics of the new variety. The present variety first fruited in 1954 at the Experimental Vineyard, University of California, Davis, Calif.

The objective in producing this new variety was to combine many of the desirable viticultural features of the Carignane and Grenache, but improve the color, flavor and aging ability of the wine. Most premium red wines attain their fullest quality and complexity after many years of aging.

The Vine: The vine is only of moderate vigor, the canes semi-procumbent, but it produces many leafy shoots capable of maturing a large crop. A very high proportion of the buds are fruitful so that systems of short pruning are recommended. Yields are in the range of 10 to 12 tons per acre without overcropping or reduction of wine quality.

Shoot tip: (10″–12″) Unfolding leaves suffused pink at borders, becoming dark green, not bronzed, short internodes, young leaves when half expanded have shiny pebbled surface, completely covered with arachnoid hairiness, flower clusters borne on nodes 2, 3, and 5.

Figure 1:
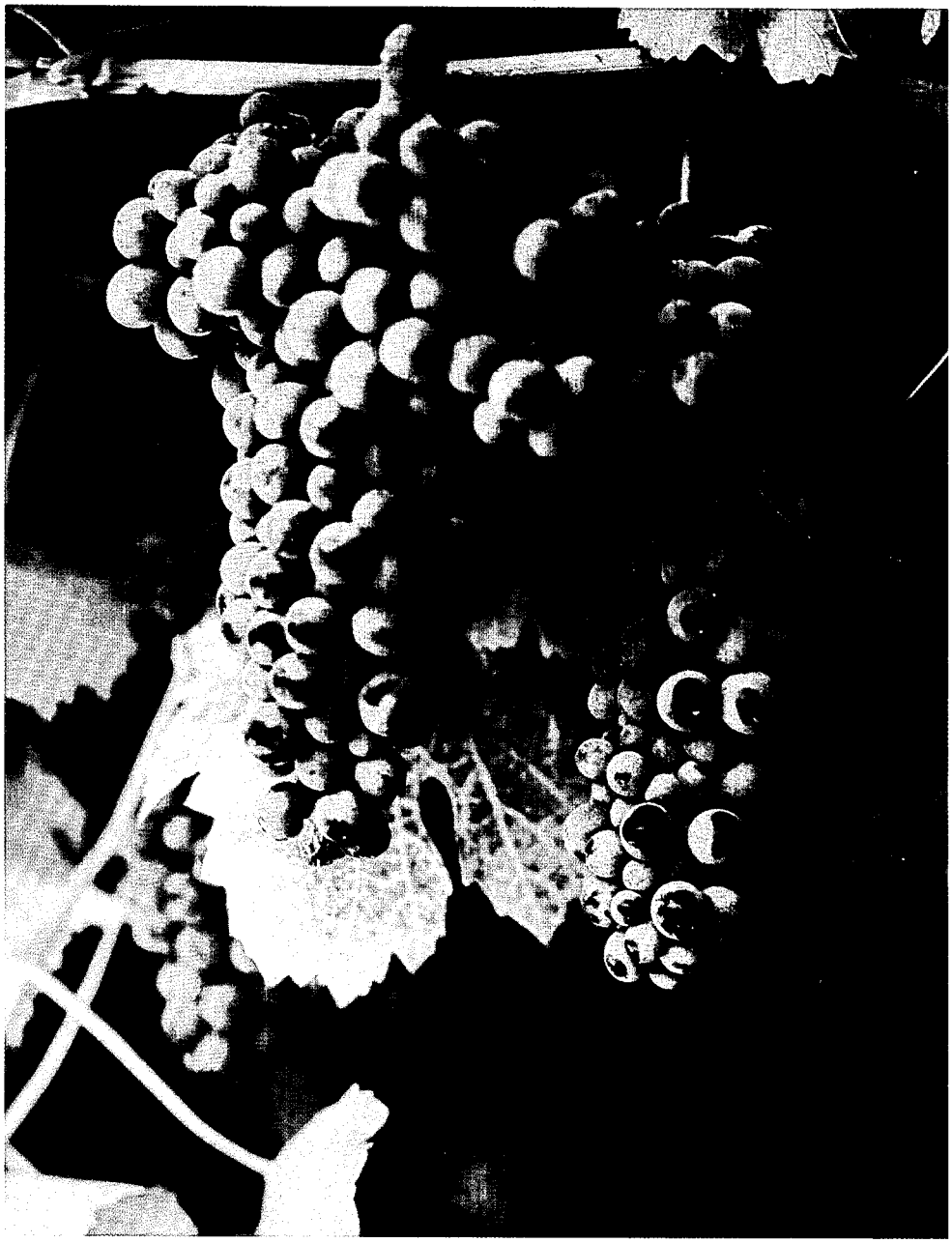
FIG. 1 is a view of a typical cluster and stem of the new variety.
Figure 2:
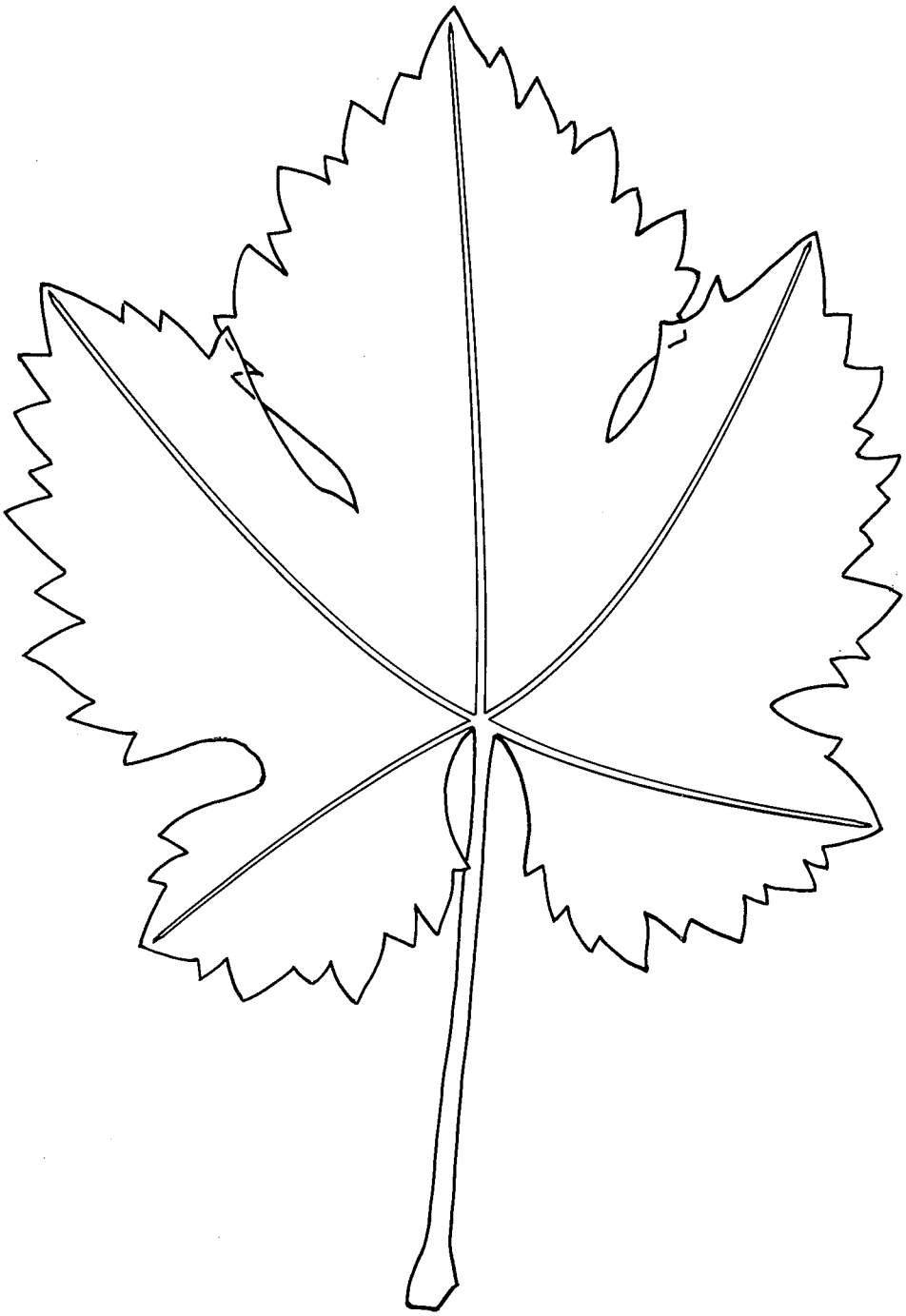
FIG. 2 illustrates in outline form a typical leaf of the new variety.

Leaf: (See FIG. 2) Medium in size, 5-lobed, the central lobe triangular and apex shortened, apices of lateral lobes projecting well beyond the border outline, longer than wide, 17.6 x 16.6 cm.; upper sinuses deep, halfway to midrib, narrow, V-shaped, closed only at summit by overlapping lobes; lower sinuses well marked, very wide, open, U-shaped; petiolar sinus open, wide U-shaped, petiole long, medium thick, vinous red, color extending part way up principal veins, sparsely arachnoid hairy on veins only; teeth large, in two series, on the lower lobes the largest are obtuse, very broad and rounded.

Canes: Light brown, slightly ridged, nodes very dark brown in contrast, slender, long, arching, with a few secondary branches persistent and producing some second crop, round in cross section, internodes offset, tendrils very thin, wiry; buds large, very prominent, not well sealed, white wooly at apex.

The cluster: The cluster is long conical, 11.5 x 17.0 cm., unbranched but with occasional small wing, medium size, 281 g., loose to well-filled, average of 179 berries on main rachis with 14 on wing, usually 2 to 3 per cane, fruit set regular but characteristically interspersed with a few green and immature shot berries at the time of harvest, second cluster almost as large as primary; cluster stem at right angle to cane, green at maturity but tough, 5.5 cm. long, rachis flattened after first branch. Berry similar to Carignane in size, shape and appearance, juicy; pedicel tapered with large warty torus, brush very short and slender, purplish.

Berry skin, flesh color and flesh texture resemble that of Carignane.

The fruit is ready for harvest from the middle to the end of September in the San Joaquin Valley. The variety has been tested in trial blocks at Davis, Lodi, Modesto, Madera and Fresno, Calif. since 1969. The fruit reaches a high sugar content, often over 24 percent, yet the acidity remains high, 0.76 to 0.94 (as percent tartaric). The average pH of the juice is 3.34. The experimental wines have been exceptional in quality, having high color, heavy body and excellent flavor. The wines improve markedly with bottle aging. Port type wines are also rated excellent, so the variety may serve a dual purpose in wine production.

The variety: The distinctive features of the variety are heavy yield, producing fruit of high sugar content and also high acidity, especially when grown in hot grape growing regions, such as the San Joaquin Valley of California. It is a dual purpose variety producing dry table wines of deep red color, and excellent flavor, capable of aging to a superior product. It is also an excellent variety for the production of port type wines.

I claim:

1. The new and distinct variety of grapevine herein described and illustrated and identified by the characteristics enumerated above.

No references cited.

ROBERT E. BAGWILL, Primary Examiner